US005792660A

United States Patent [19]
Spillert et al.

[11] Patent Number: 5,792,660
[45] Date of Patent: Aug. 11, 1998

[54] COMPARATIVE DETERMINANTS OF VISCOSITY IN BODY FLUIDS OBTAINED WITH PROBES PROVIDING INCREASED SENSITIVITY

[75] Inventors: Charles R. Spillert, West Orange; Eric J. Lazaro, Jersey City, both of N.J.

[73] Assignee: University of Medicine and Dentistry of New Jersey, Piscataway, N.J.

[21] Appl. No.: 720,675

[22] Filed: Oct. 2, 1996

[51] Int. Cl.⁶ .................................................. G01N 33/86
[52] U.S. Cl. .................. 436/2; 436/54; 436/63; 436/69; 422/61; 422/73; 600/368; 600/369; 73/54.01; 73/54.02; 73/54.24; 73/54.27; 73/54.41
[58] Field of Search .................. 436/2, 54, 63, 436/69, 70; 73/54.01, 54.02, 54.04, 54.07, 54.24, 54.27, 54.41, 64.41, 64.42; 128/637; 422/61, 73, 100; 600/368, 369

[56] References Cited

U.S. PATENT DOCUMENTS

| | | | |
|---|---|---|---|
| 3,587,295 | 6/1971 | Simons | 73/64.42 |
| 3,741,002 | 6/1973 | Simons | 73/64.53 |
| 4,026,671 | 5/1977 | Simons et al. | 422/73 |
| 4,083,363 | 4/1978 | Philpot, Jr. | 128/637 |
| 4,341,111 | 7/1982 | Husar | 73/64.42 |
| 4,705,756 | 11/1987 | Spillert et al. | 436/64 |
| 4,814,247 | 3/1989 | Spillert et al. | 436/69 |
| 4,900,679 | 2/1990 | Spillert et al. | 436/69 |
| 4,947,678 | 8/1990 | Hori et al. | 73/54.42 |
| 5,108,403 | 4/1992 | Stern | 606/93 |
| 5,138,872 | 8/1992 | Henderson | 73/64.41 |

OTHER PUBLICATIONS

Chandler et al. (1986) Clin. Chem. 32:505–7.
Linderkamp et al. (1992) Pediatr. Res. 32:97–102.
Pries et al. (1992) Am. J. Physiol. 263:H1770–8.

*Primary Examiner*—Maureen M. Wallenhorst
*Attorney, Agent, or Firm*—Klauber & Jackson

[57] ABSTRACT

This invention involves a method of analyzing a body fluid such as blood from a patient to determine whether or not there is a significant difference or change in the comparative determinants of viscosity in the body fluid sample, the comparative determinants being derived using a probe which provides increased sensitivity and corresponding improved relative viscosity values when used together with a suitable viscosity device, in order to identify the presence or incipiency of a symptomatic or asymptomatic pathology caused by or leading to said differences or changes in viscosity.

45 Claims, 2 Drawing Sheets

FIG. 2

COMPARATIVE DETERMINANTS OF VISCOSITY IN BODY FLUIDS OBTAINED WITH PROBES PROVIDING INCREASED SENSITIVITY

FIELD OF THE INVENTION

The present invention is in the field of methods and devices, especially diagnostic test kits, for measuring properties of body fluids, especially hematologic fluids, particularly such methods and devices used to determnine the viscosity of whole blood samples from mammals in order to determine the existence or incipience in said mammals of a pathological state or condition, or in order to monitor a known pathological state existing in said mammals.

BACKGROUND OF THE INVENTION

The present invention is concerned with the viscosity characteristics of body fluids, i.e., an exudate or transudate comprising cerebro-spinal fluid, drainage fluid from one or more body organs or natural or adventitious cavities, or an hematologic fluid, especially whole blood, plasma or serum, especially the interrelationships and variations of the determinants of viscosity under different testing protocols, especially those involving probes which provide increased sensitivity and correspondingly improved comparative viscosity values for samples being tested; especially comparative values from one patient or subject population to another, or in the same patient or subject population after it has undergone a challenge to homeostasis such as disease, especially infection, or surgery. The viscosity values may reveal states of hypoviscosity or hyperviscosity, i.e., altered resistance to flow caused by abnormally low or high viscosity levels, respectively, or viscosity values more typical of normal states or those found in a normal population. It is the comparative or relative differences between these values and the comparative or relative changes which these values undergo which are of importance in the present invention. These interrelationships and variations are referred to herein as the "comparative determinants of viscosity". These abnormal values, obtained and interpreted by the methods and devices of the present invention, become useful identifiers of existing disease states and valuable predictors of the onset of pathology.

Viscosity of Body Fluids

It is known generally that determination of a viscosity change occurring in body fluids, especially blood or other hematologic fluids, is important in assessing the actual condition of such body fluid, blood or other hematologic fluid, for example, it enables a blood property to be readily determined. Abnormal viscosity values can be used to diagnose and quantitate the severity of so-called hyperviscosity diseases such as sickle cell disease, diabetes, cerebral infarction, i.e., stroke, and myocardial infarction, i.e., heart attack. The physical variables which control the flow of body fluids, especially blood flow dynamics in vivo, such as perfusion pressure, flow rate, and the diameter of the elastic vessels carrying the blood, can frequently be determined by in vitro procedures. For example, it has been found that blood viscosity increases exponentially with increasing hematocrit, but that the slope of this curve decreases, i.e., viscosity is altered, with decreasing blood vessel diameter. The apparent blood viscosity depends not only on the hematocrit, plasma protein concentration and temperature, but also on the shear forces applied by, and the geometrical design and other structural features of the instrument which is used to measure that viscosity. For example, when measured in rotational viscometers, apparent blood viscosity increases in a nonlinear fashion with increasing hematocrit, and qualitatively similar behavior has been found in glass tube viscometers down to a diameter of ~9 μm. In smaller diameter tubes, however, the relationship between viscosity and hematocrit appears to be linear: and a hypothetical explanation for this behavior can be deduced from available knowledge of the hematocrit and diameter dependencies of erythrocyte arrangement in tubular flow. In tubes such as capillaries which are <6 μm in diameter, erythrocytes travel in a single-file flow pattern regardless of the hematocrit, since only one normal cell can be accommodated in such cross-sections. Such red blood cell accommodation is possible because this type of cell can alter its shape and thus negotiate smaller sized vessels. In capillaries or non-capillary tubes of larger diameter, i.e., the macrocirculation, on the other hand, multi-file flow conditions prevail at higher hematocrit levels. While viscosity increases will be linear at low hematocrits, i.e., arithmetical, above a certain hematocrit threshold level, viscosity will increase geometrically.

Blood viscosity measurements made according to methods known in the art have been used as crude diagnostic aids to physicians, because of their frequent lack of predictability. For example, it has been observed that during the acute phase of myocardial infarction, i.e., onset up to 24–48 hours thereafter, blood viscosity of the patient is likely to change. This supports a growing concern as to the appropriate therapy. However, patients who have previously suffered a myocardial infarction at a later point in time tend to exhibit higher blood viscosity values than normal levels, indicating drug therapy such as anticoagulants or the like to reduce the viscosity to a more normal level.

By contrast, the blood viscosity values determined by the methods described herein using probes which provide increased sensitivity, are an accurate reflection of the changes talking place in the blood, expressed as a continuum from the normal or fast flowing phase to the slow flowing phase; and therefore are of significantly improved value in indicating a change in the patient's blood toward a hypo- or hyperviscous state, and thus toward a fast or slow flowing phase, with predictable consequential results in the cardiovascular system of the patient. Thus, natural and dynamic viscometric determinations can serve as indicators of desirable therapeutic choices.

The devices and methods of the present invention provide information of critical importance to the diagnosis and treatment of various pathologies, and offer a number of significant advantages over devices and methods utilized heretofore. One specific and beneficial use of the present invention is in connection with studies of blood and blood components in fields of study where the use of modern drugs that thin or thicken the blood have been hampered by the absence of means for determining the pre-existing viscosity of said blood and for further determining the prospective viscosity thereof after the administration of specific drugs. The present invention provides means for determining the viscosity characteristics of whole blood samples or samples of blood components. With establishment of the initial and acquired viscosity characteristics the medical practitioner can more efficiently determine a course of treatment and drug administration.

The devices of the present invention can provide information relating to critical characteristics of various body fluids, whether they are exudates or transudates, typically including cerebro-spinal fluid, drainage fluid from one or more body organs or natural or adventitious cavities, or an hematologic fluid, especially whole blood, plasma or serum. The devices are intended to provide data on the relative viscosity of such fluids, especially blood and other hematologic fluids so that response times, mechanical properties or preferred treatment procedures may be expediently determined and regulated. Another important use of the present invention is to study body fluids, which are exudates or transudates comprising cerebro-spinal fluid, drainage fluid from one or more body organs or natural or adventitious cavities, or an hematologic fluid, especially whole blood, plasma or serum, in which the relative viscosity values thereof and changes in those values may be indicative of deficiencies in general health, digestion, blood circulation rates, dehydration and other factors that are dependent upon the fluid circulation capabilities of the body.

BRIEF DESCRIPTION OF THE PRIOR ART

U.S. Pat. No. 3,741,002 to Simons discloses a test apparatus and method for providing data on the shear modulus and rheology characteristics of the fluid sample. The fluid is subjected to a mechanical energy input after which the intensity of the energy transmitted by the fluid is measured, which in turn provides a measurement of the coupling efficiency existing between an excitation rod or probe and the fluid sample. By determining the balance or proportion of energy levels at input and at the readout, this coupling efficiency and/or other changes in the characteristics of the fluid sample may be obtained. When these changes are correlated over a period of time, additional and important information relating to the sample is obtained.

U.S. Pat. No. 4,083,363 to Philpot describes an apparatus for determining blood viscosity in the body on an in vivo basis, and suggests that the values obtained thereby can be compared to those obtained from various groups of individuals, thereby providing the basis for diagnostic determinations and evaluations.

U.S. Pat. No. 4,341,111 to Husar discloses apparatus and methods for determining the viscoelastic characteristics of fluids which is based on an electromagnetic oscillation drive with phase shifted triggering of current flow that provides an even oscillation stimulation. The fluid specimen is acted upon by the wall of an oscillating body and responds depending on its viscoelastic properties.

U.S. Pat. No. 4,814,247 to Spillert et al. describes a method for discovering or monitoring a pathological condition in a mammal in which a cellular and chemical modulator is admixed with a cellular hematological fluid sample from said mammal, after which a reaction parameter is determined and compared to a similar parameter from a mammal of known healthy state. The reaction parameter is preferably a clotting parameter measured as fibrin levels or as a function of a time differential between fibrin levels. U.S. Pat. No. 4,900,679 to Spillert et al., contains a similar disclosure.

U.S. Pat. No. 4,947,678 to Hori et al. is concerned with a method for measuring viscosity changes in blood using a sensor comprising an endothermic or exothermic element disposed in a blood sample, after which the blood is stimulated to cause clotting and the change in viscosity is measured based on changing temperature values detected by said sensor.

U.S. Pat. No. 5,138,872 to Henderson discloses a fluid viscoelastic test apparatus comprising probe means, electromechanical transducer means, drive circuitry for providing a drive signal for generating oscillatory mechanical displacement of said probe means, response circuitry for monitoring response signals which are representative of one or more viscoelastic properties of said fluid and forming a feedback loop with the drive circuitry, circuit means for regulating an amplitude of a first signal within said feedback loop, microcontroller means for receiving and analyzing the response signals to determine the one or more viscoelastic properties of said fluid, and digital output means.

Linderkamp, et al., "Blood Viscosity and Optimal Hematocrit in Preterm and Full-Term Neonates in 50- to 500-μm Tubes", *Pediatr. Res.*, 32(1), 97–102 (1992), contains a study of erythrocyte transport efficiency (hematocrit/blood viscosity) which was used to estimate the optimal hematocrit.

Pries, et al., "Blood Viscosity in Tube Flow: Dependence on Diameter and Hematocrit", *Am. J. Physiol.*, 263, H1770–1778 (1992), contains a study which provides a comprehensive data base for the description of relative apparent blood viscosity as a function of tube diameter and hematocrit.

Chandler and Schmer, "Evaluation of a New Dynamic Viscometer for Measuring the Viscosity of Whole Blood and Plasma", *Clinical Chemistry*, 32(3), 505–507 (1986), describes an evaluation of the SONOCLOT® Analyzer for use in measuring the viscosity of whole-blood and plasma, and application of the information obtained to monitoring patients with hyperviscosity syndromes such as multiple myeloma.

SUMMARY OF THE INVENTION

In accordance with the present invention there is provided a method of analyzing one or more samples of a body fluid from a mammal by determining whether or not there is a significant difference or change in the comparative determinants of viscosity in the body fluid sample of the mammal, the comparative determinants being derived using a probe which provides increased sensitivity and correspondingly improved relative viscosity values for samples being tested when used together with a suitable measuring device, in order to identify the presence or incipiency of a symptomatic or asymptomatic pathology caused by or leading to said differences or changes in viscosity, comprising: (1) placing a first aliquot of the body fluid sample in a suitable container, optionally together with a vehicle, to be used as a control aliquot; (2) placing a second aliquot of the body fluid sample in a suitable container, optionally together with a vehicle, to be used as an active aliquot; (3) measuring relative viscosity of the control and active aliquots and obtaining data which are comparative determinants of viscosity by using a probe which provides increased sensitivity and correspondingly improved relative viscosity values for the aliquots being measured when used together with a suitable measuring device; and (4) identifying the presence or incipiency of said symptomatic or asymptomatic pathology caused by or leading to said differences or changes in viscosity, by analysis of the comparative determinants of viscosity obtained as recited above for the control and active aliquots, wherein the values for the control and active aliquots are obtained (i) at different times from the mammal, (ii) under conditions of significantly changed homeostasis of the mammal, (iii) in the absence and/or presence of, respectively, a viscometric modulator, or (iv) from the same mammal in a healthy state, free of the pathology, and from the mammal being tested, respectively, or any combination of the above testing circumstances.

There is further provided the above-described method of the present invention wherein the probe which provides increased sensitivity and correspondingly improved relative viscosity values for samples being tested, when used together with a suitable measuring device, comprises a hollow tube of glass, ceramic, plastic or metal, the end thereof which enters the aliquot to be measured, having been sealed with bone wax or dental wax. In particular, there is provided a probe comprising a hollow tube of plastic, the end thereof which enters the aliquot to be measured, having been sealed with bone wax.

There is further provided a method as recited above wherein said body fluid is an exudate or transudate comprising cerebro-spinal fluid, drainage fluid from one or more body organs or natural or adventitious cavities, or an hematologic fluid, especially whole blood, plasma or serum; and further wherein the suitable measuring device is a SONOCLOT® Analyzer.

Where the above-recited method is carried out using whole blood as the body fluid sample, it may additionally comprise placing an anticoagulating agent and/or a viscometric modulator together with the active aliquot in a suitable container, optionally together with a vehicle;

thereafter incubating said control and said active aliquots at from about 35° C. to about 40° C. for from about 1 to about 20 minutes, preferably for from about 5 to about 10 minutes; and then measuring the relative viscosity of the control and active aliquots using the probe with increased sensitivity. Where an anticoagulating agent is not utilized, it will be necessary to measure the relative viscosity within from about 0.1 to about 1.0 minute after said whole blood sample has been withdrawn from said mammal.

Where a viscometric modulator is added as described above, it will be present in a concentration of from about 10 μg/ml to about 50 μg/ml of said active aliquot, and comprises one or more members selected from the group consisting essentially of viscometric modulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities. Said viscornetric modulator is particularly an endotoxin or a collagen.

Where the above-recited method involves whole blood as the body fluid sample, it may be carried out without prior anticoagulation treatment of the sample in those situations where there is immediate access to the measuring device of the present invention. However, there is also provided in accordance with the present invention the above-recited method wherein said aliquots of whole blood are anticoagulated and are prepared by mixing said whole blood with an anticoagulating agent selected from the group consisting of sodium citrate, sodium oxalate, heparin and EDTA.

The above-described method utilizing anticoagulation of the whole blood sample may also additionally comprise placing a viscometric modulator together with said second aliquot in a suitable container, optionally together with a vehicle. The viscometric modulator will be present in a concentration of from about 10 μg/ml to about 50 μg/ml of said active aliquot, and will comprise one or more members selected from the above-described group.

Further in accordance with the present invention, for the above-described methods the optional vehicle particularly comprises a physiological saline solution; the mammal is *homo sapiens*; and the incubation of the control and active aliquots is carried out at about 37° C.

In accordance with the present invention there is still further provided a prepackaged diagnostic kit for use together with a suitable device for analyzing one or more samples of a body fluid to be taken from a mammal for determination of whether or not there is a significant difference or change in the comparative determinants of viscosity in the body fluid sample of the mammal, the comparative determinants being derived using a probe which provides increased sensitivity and correspondingly improved relative viscosity values for samples being tested, when used together with a suitable measuring device, in order to identify the presence or incipiency of a symptomatic or asymptomatic pathology caused by or leading to said differences or changes in viscosity, comprising: (1) at least one first container and at least one second container suitable for receiving aliquots of the one or more samples of body fluid to serve as control and active aliquots, respectively, for measuring relative viscosity when used together with said suitable measuring device, and for obtaining data which are comparative determinants of viscosity for the control and active aliquots; (2) a probe which provides increased sensitivity and correspondingly improved relative viscosity values for the aliquots being measured, when used together with a suitable measuring device; and (3) a diagnostic protocol for identifying the presence or incipiency of said symptomatic or asymptomatic pathology caused by or leading to said differences or changes in viscosity, comprising means for analysis of the comparative determinants of viscosity obtained as recited above for the control and active aliquots, wherein the values for the control and active aliquots are obtained (i) at different times from the mammal, (ii) under conditions of significantly changed homeostasis of the mammal, (iii) in the absence and/or presence of, respectively, a viscometric modulator, or (iv) from the same mammal in a healthy state, free of the pathology, and from the mammal being tested, respectively, or any combination of the above testing circumstances.

There is further provided the above-described prepackaged diagnostic kit of the present invention wherein the probe which provides increased sensitivity and correspondingly improved relative viscosity values for samples being tested, when used together with a suitable measuring device, comprises a hollow tube of glass, ceramic, plastic or metal, the end thereof which enters the aliquot to be measured, having been sealed with bone wax or dental wax. In particular, there is provided a probe comprising a hollow tube of plastic, the end thereof which enters the aliquot to be measured, having been sealed with bone wax.

There is still further provided the above-described prepackaged diagnostic kit of the present invention wherein said body fluid is an exudate or transudate comprising cerebro-spinal fluid, drainage fluid from one or more body organs or natural or adventitious cavities, or an hematologic fluid, and particularly wherein the hematologic fluid is whole blood; and wherein the suitable measuring device is a SONOCLOT® Analyzer. Further, where whole blood is the body fluid, there is provided a prepackaged diagnostic I-it wherein at least one of the first containers has a predetermined amount of a preselected anticoagulating agent therein for preparing one or more anticoagulated aliquots of the whole blood sample to serve as control aliquot(s), optionally containing a vehicle therefor; at least one of the second containers has a predetermined amount of the preselected anticoagulating agent therein for preparing one or more anticoagulated aliquots of the whole blood sample to serve as active aliquot(s), optionally containing a vehicle therefor; and the diagnostic protocol recites incubating said control and said active aliquots at from about 35° C. to about 40° C. for from about 1 to about 20 minutes, preferably for from about 5 to about 10 minutes. There is further provided the above-described prepackaged diagnostic kit of the present invention wherein the preselected anticoagulation agent is one or more members selected from the group consisting of sodium citrate, sodium oxalate, heparin and EDTA; the second containers additionally comprise a predetermined amount of a preselected viscometric modulator for use together with the active aliquot, optionally together with a vehicle, wherein the viscometric modulator in the second container is present in a concentration of from about 10 µg/ml to about 50 µg/ml of anticoagulated whole blood, and wherein the viscometric modulator comprises one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities, especially wherein the viscometric modulator is an endotoxin or a collagen.

A viscometric modulator may be included with those prepackaged diagnostic -kits of the present invention which do not provide for anticoagulation of the whole blood sample. In such prepackaged diagnostic kits the second containers may additionally comprise a predetermined amount of a preselected viscometric modulator for use together with the active aliquot, optionally together with a vehicle, and the viscometric modulator will be present in a concentration of from about 10 µg/ml to about 50 µg/ml of anticoagulated whole blood. A predetermined amount of the preselected viscometric modulator may also be provided as a coating on the probe to induce relative viscosity changes in the sample being measured. The preselected viscometric modulator may also be provided in a separate container from which it may be applied to and coated on the probe. Further, the viscometric modulator comprises one or more members selected from the above-described group.

There are further provided prepackaged diagnostic kits of the present invention wherein the optional vehicle comprises a physiological saline solution which may be present in the first and second containers or may be present in a separate, additional container for dispensing to the first and second containers; the diagnostic protocol indicates that incubation of the control and the active aliquots is to be carried out at about 37° C. and there is optionally provided in the kit a heating means for obtaining and maintaining the incubation temperature.

There is further provided the above-described prepackaged diagnostic kits wherein the diagnostic protocol recites that where an anticoagulating agent is not utilized, it will be necessary to measure the relative viscosity within from about 0.1 to about 1.0 minute after said whole blood sample has been withdrawn from said mammal, and further indicates that the step of incubating the control aliquot and the active aliquot is to be carried out for from about 1 to about 20 minutes.

There is still further provided an improved probe which provides increased sensitivity and correspondingly improved relative viscosity values for a sample of a body fluid being measured, when used together with a suitable measuring device, comprising a hollow tube of glass, ceramic, plastic or metal, the end thereof which enters said sample to be measured, having been sealed with bone wax or dental wax. In particular there is provided the improved probe wherein the suitable measuring device is a SONO-CLOT® Analyzer; the body fluid is whole blood; and the probe additionally has coated thereon a predetermined amount of a preselected viscometric modulator before being introduced into said sample to be measured, wherein the viscometric modulator has previously been coated on the probe, or wherein the viscometric modulator is provided in a separate container from which it is then applied to and coated on the probe.

DETAILED DESCRIPTION OF THE INVENTION

One way of achieving the objects of the present invention is by determining whether or not there is a significant difference in the comparative determinants of viscosity in one or more samples of a body fluid which is an exudate or transudate comprising cerebro-spinal fluid, drainage fluid from one or more body organs or natural or adventitious cavities, or an hematologic fluid, especially whole blood, plasma or serum, wherein the comparative determinants are derived using a probe which provides increased sensitivity and correspondingly improved relative viscosity values for the samples being tested, when used together with a suitable measuring device. The final step of identifying the presence or incipiency of a symptomatic or asymptomatic pathology caused by or leading to the differences or changes in viscosity measured by the probe which provides increased sensitivity, is achieved by analysis of the comparative determinants of viscosity for the control and active aliquots, wherein the values for the control and active aliquots are obtained (i) at different times from the mammal, (ii) under conditions of significantly changed homeostasis of the mammal, (iii) in the absence and/or presence of, respectively, a viscometric modulator, or (iv) from the same mammal in a healthy state, free of the pathology, and from the mammal being tested, respectively, or any combination of the above testing circumstances.

The methods of the present invention also have the advantage of being very rapid. Where the body fluid is whole blood, the methods of the present invention do not even require that an anticoagulating agent be used, and they are, consequently, highly advantageous in medical care facilities such as operating rooms, emergency rooms, intensive care units, and ambulances that can make a whole blood sample from a patient immediately available for analysis, before natural clotting has time to take place. Indeed, under such circumstances, the addition of an anticoagulating agent would be superfluous and time consuming. It is only necessary that the apparatus required to carry out the test procedure be near the patient and available at the time the whole blood or other body fluid sample is taken from the patient for testing.

Comparative Determinants of Viscosity

As indicated, in one embodiment of the present invention, the comparative determinants of viscosity are obtained by using whole blood samples without any added anticoagulant or viscometric modulator. The comparative measurements are based on the readings from a probe which provides increased sensitivity and correspondingly improved relative viscosity values for the samples being tested, when used together with a suitable measuring device. The readings thus obtained must, however, also be compared to those from the same patient wherein the whole blood sample has been taken at a different time. For example, where a patient suffering from chest pains and suspected of having a myocardial infarction, is brought to a hospital emergency room in an ambulance, a series of whole blood samples will be withdrawn from the patient at predetermined, or even random but measured time intervals. Using the probe which provides increased sensitivity, along with the other procedures and devices of the present invention, relative viscosity determinations are made on the blood samples, which ultimately provide a graph of the changing relative viscosity values thus measured over time. This graph becomes the "signature" of the changing ability of the patient's heart muscle to move blood through the patient's circulatory system, and thus a useful diagnostic and prognostic tool.

Other comparisons of relative viscosity values are similarly useful. For example, the differences in these values, obtained under conditions of significantly changed homeostasis in the patient, may be analyzed in order to provide valuable information about the response of the patient's body to the stimuli or challenges involved. These stimuli and challenges may consist of acute and chronic diseases which are infectious, autoimmune or congenital in origin; various types of trauma to which the patient's body may be subjected, including invasive surgery; and therapeutic agents of all sorts and administrative routes, including vaccines, pharmaceuticals, chemotherapeutics, and radiation treatments. Using the probe which provides increased sensitivity, relative viscosity determinations are made on the blood samples of a patient taken before, during, and after the occurrence of such stimuli and challenges, which ultimately provide a graph of the changing relative viscosity values with the changing homeostasis of the patient. This graph becomes the "signature" of the changing response of the patient's body, and thus a useful diagnostic and prognostic tool. For example, a comparison of the relative viscosity values thus obtained from a patient's whole blood samples on a preoperative and then on a postoperative basis, provides an accurate guide to the likelihood that the patient will experience a pulmonary or other embolism as a result of the surgical trauma.

Still further comparisons of relative viscosity values are useful, and include, for example, the differences in these values obtained in the absence and/or presence of a viscometric modulator as defined herein. The large number and variety of such viscometric modulators, and the significantly different types of activity which they exhibit in the body of a patient, as reflected in changes in the relative viscosity values of whole blood samples taken from the patient, provide a significant basis upon which to establish diagnostic and prognostic profiles for the patient, as described in more detail further below.

One of the most important analyses of relative viscosity values which can be made in accordance with the present invention, is a comparison of those values obtained from a patient with those from the same mammal in a healthy state, free of the pathology from which the patient being tested suffers or is suspected of suffering. And finally, any combination of the above testing circumstances may be employed. For example, the presence and/or absence of viscometric modulators may be combined with changes in homeostasis, and the values thus obtained may be compared, in turn, to values obtained from "normal" patients, i.e., patients in which the pathology being tested for does not exist or is not incipient. The changes, interrelationships and variations in these relative viscosity values comprise the comparative determinants of viscosity as defined in the present invention.

In another embodiment, relative viscosity is determined by admixing a viscometric modulator as defined herein with the cellular hematologic fluid, usually a whole blood sample, of the mammal and determining the relative viscosity as measured by a probe which provides increased sensitivity, and comparing the viscosity values thus obtained with viscosity values obtained with respect to control samples, which may be samples from the same patient where a viscometric modulator is not added, samples from the same patient taken at different times or changes in homeostasis, with or without viscometric modulators present, as well as normal samples, i.e., hematological fluids of mammals of known healthy states, in the presence and/or absence of the same or a substantially similar viscometric modulator.

As used herein, the term "cellular hematologic fluid of a mammal" is intended to mean the whole blood thereof or a fraction thereof, including monocytes and other cellular or noncellular components of the mammal. The term "mammals" as used herein includes *homo sapiens*, and domesticated animals, e.g. race horses and cattle.

As used herein, the term "vehicle", with which the aliquots of body fluid samples, viscometric modulators, anticoagulant agents, and other components of the methods of the present invention may optionally be admixed, comprises any of those well known solvents and suspending media used by the artisan in determinations of relative viscosity values of various test compositions. Preferably, these vehicles have a small, or at least determinable impact on the relative viscosity values of the test composition, and are substantially inert with respect to the test composition. However, the known ability of various solvents to alter the properties of cellular membranes, allows them to impact the relative viscosity of whole blood samples in particular, and as such the vehicle may effectively become a viscometric modulator as defined herein. The choice of vehicle will depend largely on the solubility characteristics of the test composition. Where the test composition is water soluble, the vehicle is preferably physiological saline. Other useful solvents, e.g., dimethyl sulfoxide (DMSO) and other well known polar and non-polar solvents, are well known to the artisan, who can select a suitable candidate for use by the application of ordinary skill and the information provided herein.

As used herein, the term "viscometric modulator" is intended to mean an agent, whether isolated in a substantially pure form, exogenously or endogenously derived, as a product of living cells on an in vivo or in vitro basis, whether naturally expressed or expressed as the product of recombinant genetic material introduced therein; or whether derived as the product of chemical or biochemical synthesis; which is the initiating or causative agent responsible for changes in the comparative determinants of viscosity which are measured by the devices and methods of the present invention. The viscometric modulator may comprise one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities, especially wherein said viscometric modulator is an endotoxin or a collagen. In particular, it is preferred that the viscometric modulator is an immunoactivator or immunoattenuator, which is an agent that either promotes or accelerates, or retards or attenuates, respectively, viscosity of whole blood or fractions thereof.

Viscometric modulators include, inter alia, endotoxins, measles and other viruses, various interferons, phorbol esters, collagens, anticoagulants such as warfarin, platelet activating factors, carrageenans, adjuvant peptides, thromboplastins, antigens, myelin, gram negative bacteria, lectins such as Concanavalin-A, and mitogens such as pokeweed mitogen. Low density lipoproteins (LDL's) have been related to increased risk of coronary heart disease and atherosclerosis due to their role in facilitating fatty deposits on artery walls; whereas, high density lipoproteins (HDL's) have the opposite or protective activity. The fact that these substances produce significant changes in relative viscosity values of whole blood samples measured in accordance with the present invention, suggests that these substances will be of value as viscometric modulators as defined herein. It is hypothesized that the alterations in relative viscosity values induced by these viscometric modulators, in patients with existent or excipient cardiovascular disease, will be significantly greater or smaller than the alteration in the relative viscosity values in normal patients, i.e., patients at low risk for cardiovascular disease.

While the mechanism of action of the present invention is not fully understood, and the scope of the present invention should not be bound by any particular theory thereof, it is believed that the body fluid viscosity characteristics of a mammal having certain pre-existing pathological states or conditions, especially with regard to whole blood in response to a viscometric modulator as defined herein, are different from the viscosity characteristics of the body fluids of healthy mammals, especially whole blood in response to the same or a substantially similar viscometric modulator as defined herein. Further, it is believed that the differences in these viscosity characteristics become even more highly contrasted and are thereby induced to yield even further information regarding pre-existing pathological states, when they are measured using a probe which provides increased sensitivity and correspondingly improved relative viscosity values for the samples being measured. Further, while monocytes to varying degrees are involved in the immune response system of the hematologic fluid to the viscometric modulator, it is believed that the immune response system involves an interaction between the monocytes and other components, e.g., T-cells, lymphocytes, neutrophils, etc. in the cellular hematologic fluid.

The pathological states and conditions, the nonspecific and even existence of which are identified by the methods and devices of the present invention include cancer; sepsis and infection; HIV infection and AIDS; diabetes; multiple sclerosis; acute myocardial infarction and other aspects of cardiovascular disease; trauma; vascular thrombosis, stroke and related pathologies; and any pathological state or condition affecting the immune response system of a mammal. It will be appreciated by one of ordinary skill in the art that a specific pathological state or condition in a test mammal can be asserted to exist to a high degree of probability after a positive determination of such existence has been made in accordance with the methods of the present invention.

Blood is able to flow freely through the body of a mammal because it is characterized by a value within an appropriate range for a fundamental property of all flowing liquids, i.e., viscosity. The impact of viscosity on blood flow can be understood from a basic demonstration in which two tubes of equal diameter are placed alongside each other on a slowly descending gradient, and water and honey are simultaneously introduced. The thicker, i.e., more viscous honey flows more slowly. Analogously, in order to improve the flow properties of blood, "thinners", e.g., warfarin, are administered to patients at risk for myocardial infarction. These blood thinners hinder clot formation in the blood, preventing occlusion of blood vessels in vital organs such as the heart, brain and kidneys. In the course of its circulation, the blood journeys from the heart through the body in vessels of decreasing caliber: arteries, arterioles and capillaries, then back to the heart through vessels of increasing caliber: venules and veins.

Nature of Blood Viscosity

Inherently, viscosity is that particular rheological property of a fluid or semifluid, or the alteration in shape of the suspended contents thereof caused by any substance as the result of molecular cohesion, which enables it to develop and maintain a certain amount of shear stress dependent upon the velocity of flow of the fluid or semifluid, and then to offer continued resistance to flow. Presently, most analyses which are carried out in order to determine the viscosity of a fluid or semifluid, or to determine the alteration in shape of the suspended contents thereof caused by any substance as the result of molecular cohesion, are performed in commercial and industrial laboratories on materials destined for the market place or workplace, e.g., cosmetics and pharmaceuticals for topical application, various hydrocarbon fluids, emulsions of all types, paints, foods, biologicals and other products in the course of production. By contrast, measurement of the viscosity of human blood, the most important life sustaining fluid, is seldom performed. Viscosity measurements of whole blood samples are not carried out routinely; and they are performed only infrequently when requested for the identification of specific clinical conditions. In those few instances, moreover, the viscosity determinations are carried out on serum, rather than whole blood samples, which is largely a matter of convenience and practicality, since hospitals and outpatient facilities do not have the equipment necessary for measuring the viscosity of whole blood samples. Moreover, such determinations on serum provide little useful information about the true viscosity state of the blood, because the role of the blood cells and their impact on viscosity have not been taken into account. The great clinical need for viscosity determinations which are accurate, reliable and meaningful, and the inadequacies of currently available technology which preclude laboratory technicians and others from obtaining them, have made a persuasive case for the application of the methods and devices of the present invention to this field.

The viscosity of a fluid may be viewed as the ratio of shear stress to shear rate in that fluid. This means that the shear stress is the "pushing" force, and that the shear rate, then, is the displacement per unit of time caused by that "pushing" force. When the viscosity of a fluid remains the same at all shear rates, the fluid is known as a Newtonian fluid. When the viscosity of a fluid does not remain constant, but rather changes in relation to the shear stress or shear rate, the flow characteristics of that fluid are referred to as being non-Newtonian. At low flow rates, such as those which occur in the venous system, human blood behaves like a non- Newtonian fluid; whereas at relatively high flow rates, such as those encountered in the arterial system, the flow characteristics of human blood resemble those of a Newtonian fluid. The amount of push or thrust required to commence the flow process of a fluid is defined as the yield stress. Thus, no flow of a fluid will occur below the yield stress value.

Whole blood is a highly complex fluid, comprising a liquid, plasma, in which solids such as red and white blood cells and platelets are suspended, various mineral and organic chemical agents are dissolved or suspended, and in which insoluble fluids are dispersed. Materials which are components or side products of the coagulation process and thus potentially related to incipient or existent pathology, e.g., cellular aggregates and fibrin clots, may also be suspended in the blood, while chemical substances which may or may not participate in the coagulation process may be dissolved in the blood. The red and white cells are also deformable to permit passage through the capillaries, adding an extra element of complexity. Normal blood flow becomes abnormal when blood clots form, when blood cells clump together to form aggregates, or when other blood cells are no longer deformable. The end result is thicker blood having a higher viscosity.

In order for the circulating blood to accomplish its objective of delivering oxygen and other substances essential to the metabolic needs of the organism at the tissue and cellular level, it must traverse the microcirculation without significant impedance and at a certain minimum velocity. This activity tales place in the capillaries, i.e., the microcirculation where harmful byproducts of metabolism, e.g., carbon dioxide, lactate, etc., are also exchanged and conveyed to the major organs of excretion, i.e., the kidneys and large intestine, for disposal outside of the body.

Evaluation of the velocity of blood flow is dependent upon three primary determinations, described by Poiseuille in 1846: (1) the pressure gradient along the blood vessel, (2) the diameter of the vessel lumen, and (3) the viscosity of the blood. Poiseuille's original work was carried out using Newtonian fluids in a totally artificial system. Later work in animals and man have shown that changes in blood viscosity, as measured by in vitro techniques, correlate well with changes in blood flow measured in vivo. Great emphasis must be placed on the fact that blood hyperviscosity, per se, results in an increase in peripheral circulation resistance which impairs tissue and cellular perfusion, the fundamental purpose served by the circulating blood. Increases in blood viscosity above a certain normal range result in higher peripheral circulation resistance and in turn lower cardiac output, which is almost entirely due to decreased stroke volume, rather than increased heart rate. Accordingly, a 10% increase in blood viscosity is associated with a 20% decrease in blood flow measured in vivo.

Devices for Determining Blood Viscosity

In the decade of the 1960's it was shown that abnormalities in blood viscosity exist in certain clinical conditions known to be associated with circulatory disturbances or anomalies. These clinical conditions include, among others, myocardial infarction, polycythemia, sickle cell disease, spherocytosis, diabetes, and peripheral arterial occlusive disease. While these observations created significant interest in the field, the instrumentation and analytical techniques which were used to generate the data on which these observations were based suffered from a number of substantial drawbacks. For example, one type of viscometer which was developed and still enjoys popular use is the Wells-Brookfield viscometer, or "cone and cup" instrument. However, the rotating disc in the cup containing the blood sample permits the blood to splash and scatter along the rim interface between the disc and the cup, thus leading to imprecise and inaccurate viscosity measurements. The more recent development of devices of the type represented by the SONOCLOT® Coagulation Analyzer, whose operation is described in detail further below, has eliminated this major defect of the cone and cup type instruments. In the SONOCLOT® Coagulation Analyzer, a vertically vibrating probe inside the cup holding the blood sample permits a wide space of operation without resulting in a splashing or scattering of the blood sample around the perimeter of the cup. However, as described by Chandler and Schmer in "Evaluation of a New Dynamic Viscometer for Measuring the Viscosity of Whole Blood and Plasma", *Clinical Chemistry*, 32(3), 505–507 (1986), the probes which are used in this device are hollow. In accordance with the present invention, it has been discovered that such hollow probes do not provide the sufficiently increased sensitivity and correspondingly improved relative viscosity values required by the present invention. Nevertheless, as demonstrated herein further below, the differences in relative viscosity values obtained with such hollow probes, as compared to those obtained with the probes of the present invention, can also provide useful information for diagnosis and prognosis.

Another and even more important feature of the methods and devices of the present invention not characteristic of techniques used heretofore, is the supplemental viscometry determinations which are made using viscometric modulators such as cellular activators, e.g., collagen and endotoxin, to induce: (1) increased cellular aggregation and (2) reduced cellular deformity. There is an underlying rational basis for the lack of sensitivity and accuracy in the viscometric determinations which have been carried out heretofore, which resides in the fact that in the natural, unaided state, changes in blood viscosity are often too small to be detectable, thus requiring the supplementation afforded by the addition of one or more viscometric modulators to the blood sample being tested. All of the above-enumerated changes in the blood accompany the most common conditions of endotoxemia. Consequently, the values for natural, unaided viscosity levels and for stress-induced viscosity levels can be determined accurately using the techniques and devices represented by the SONOCLOT® Analyzer, or an instrument of similar capability.

The SONOCLOT® Analyzer, available from Sienco, Inc., measures viscoelastic properties as a function of mechanical impedance of the sample being tested. Such analysis is very sensitive to early fibrin formation, thereby providing improved sensitivity and reproducibility of results. There is another device, the thrombelastograph (TEG), which can also be used for measuring viscoelastic properties; however, the TEG, unlike the SONOCLOT® device, does not claim viscometric capability.

While a number of different devices may be used to perform the viscosity measurements in accordance with the methods and devices of the present invention, certain features of these devices are preferred. For example, a fluid viscoelastic test instrument constructed in accordance with the present invention may have a hinged head assembly containing a transducer, which may simply comprise an off-the-shelf electromechanical audio speaker having a suitable impedance. A disposable probe may be removably attached to the transducer, and a disposable cuvette, adapted for holding a fluid sample, is received by a cuvette holder.

When the head assembly is in a lowered position, the probe is brought into contact with the fluid sample contained within the cuvette. A ready indicator, which may comprise a light emitting diode (LED), indicates that a platen has heated the sample to the desired temperature of about 37° C. A heating indicator, which may also comprise an LED, indicates that the temperature of the platen is below the desired temperature. A MIX/ZERO switch may be used which comprises a double pole double throw switch adapted for momentary closure in both directions. One pole generates two logic level inputs, MIX and ZERO, monitored by a microcontroller. The other pole uses only the MIX position of the MIX/ZERO switch to activate a mixing motor for ten seconds when the switch is moved to the MIX position. A liquid crystal display (LCD) is employed to report analysis results and operator prompts.

It is preferred in particular that the fluid viscoelastic test instruments of the present invention, in addition to being able to measure the physical properties which constitute the relative viscosity of a blood sample, also be able to generate a time varying graph or signature of a blood sample during the period of time over which changes in the viscosity of the blood occurs. Subsequent analysis of that signature will provide data from which it is possible to quantify the variables of viscosity change in the blood sample. A blood sample is added to the cuvette, and the MIX/ZERO switch is momentarily moved to the MIX position. A mixing motor, magnetically coupled to the mixing bar, is operated for stirring the blood sample contained in the cuvette for a preferred time period of ten seconds. After stirring has stopped, the head assembly is manually lowered, thereby inserting the disposable probe into the cuvette. The instrument remains in this configuration during analysis of the blood sample. An analog output voltage signal is typically coupled to a conventional external strip chart recorder. Automated analysis of the blood sample is performed by the microcontroller, which reports results on a display. Following analysis of a blood sample, the head assembly is raised and the disposable cuvette containing the blood sample and the disposable probe are both discarded.

Typically, the above-described disposable cuvettes are especially designed for use in the particular measuring devices commercially available. However, it is well within the skill of the artisan in this field to make the required adaptations to such a cuvette so that it can also serve the functions of the above-described vials to which the blood sample aliquots are dispensed, and which contain reactants as appropriate, e.g., an anticoagulant, a vehicle, or a viscometric modulator as defined herein.

Figure 1:
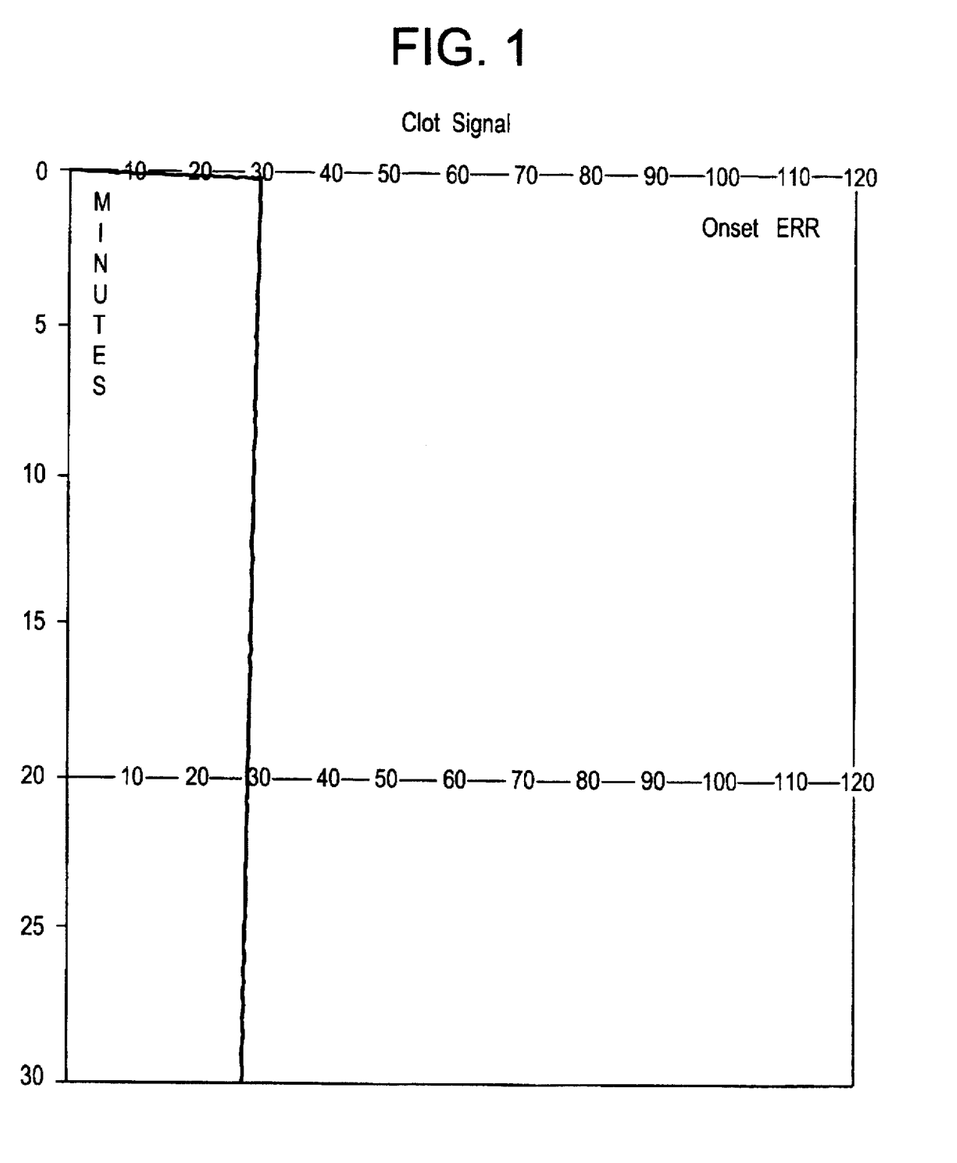
FIG. 1 depicts a graphical plot of data obtained from a SONOCLOT® Analyzer showing the relative viscosity of a whole blood sample.

A typical graphical output signal, such as would be recorded on an external strip chart recorder, would display the relative viscosity, i.e., the amplitude of the tracing. FIG. 1 demonstrates typical relative viscosity values of a sample of anticoagulated human whole blood.

It is also contemplated that the comparative significance of the relative viscosity values obtained for control and active samples as described herein, would effectively be independent of the particular viscometer or type of viscometer chosen to carry out the analysis, so long as it was carried out in accordance with the other parameters imposed by the methods of the present invention.

Probes Which Provide Increased Sensitivity and Correspondingly Improved Relative Viscosity Values The particular construction of the probe, which is preferably disposable, used in the devices of the present invention as described above is a critical aspect of the present invention. In a representative construction, the lower portion of the probe carrier is formed of a resilient material and is provided with a counterbore adapted to receive an end of an exciter rod, which is the probe itself. The exciter rod probe is of a fixed length, and accordingly, when it is introduced into the counterbore, it will extend a prescribed distance downwardly therefrom so that the free end thereof is engaged within the sample cup. With a 0.4 cc sample in the cup, the free end of the probe will be immersed in the sample. When the driving device is powered, the essentially non-elastic exciter rod-probe will be moved vertically in a vibrational mode to mechanically agitate the sample in the cup.

When used in a conventional manner, the exciter rod-probe is hollow in conformation, which facilitates accommodating and securing it in the counterbore of the probe holder. However, it has been discovered that this design feature, while regarded heretofore as adequate for measuring the viscosity of a blood sample, is not capable of measuring or determining the relative viscosity data signature of the blood sample to a sufficiently high degree of sensitivity to provide useful information regarding the condition and prognosis of the patient. By generating the relative viscosity data signatures based on increased sensitivity in accordance with the present invention, patterns of levels and/or changes consistent with a significantly increased likelihood of a present or incipient pathology, can be much more successfully pinpointed.

Heretofore, viscosity tests have been performed with instrumentation characterized by the application of a low level of force-induced energy input to the sample of blood. The probes used in the present invention, in contrast, apply high levels of force-induced energy input to the blood samples undergoing measurement. The application of high levels of force-induced energy input to blood samples is achieved with the increased sensitivity probes of the present invention. These tubular probes oscillate within the blood sample. The associated instrument detection circuitry senses the resistance to motion that the probe encounters. The data that is generated is then recorded on a printout in which the relative viscosity is plotted as the ordinate on they-axis against time as the abscissa on the x-axis.

In order to generate a higher force-induced energy input into the blood sample from the probe used with the present invention, a modified probe is provided. The probe may be modified in a number of different ways so long as it still provides a suitable increase in sensitivity in accordance with the present invention. One modification that has provided satisfactory results has been to seal the end of a hollow probe which enters the blood sample, with a relatively hydrophobic material that is sufficiently pliable to be introduced into the end of the hollow probe to a depth of about 0.5 cm, where it becomes permanently lodged. The material may have an elastic, pliable character that does not change; or it may be flexible at first, and then harden into a concrete mass in the hollow probe. Suitable materials of this type include bone wax, available from ETHICON®, and dental wax. Bone wax can be used to fill the opening of the hollow probe at room temperature, while dental wax is preferably first melted, after which the hollow probe is dipped into the wax to a depth of about 0.5 cm, and the wax-filled probe is then cooled to room temperature before being used. Bone wax itself has been demonstrated to activate cellular aggregation in whole blood samples, an event which is a precursor to hyperviscosity.

The hollow probe which is later sealed can be made of non-reactive metals such as aluminum, bronze or stainless steel, or of various glass, ceramic, or synthetic resin compositions well known to the artisan who fabricates diagnostic equipment for medical use. It is desirable that these materials be as inert as possible, in order to avoid unwanted reactions with, and of, the constituent parts of the blood sample. The varying density of these materials will have a slight, but calculable effect on the force-induced energy which they impart to the blood sample. The hollow probe imparts less force-induced energy to the blood sample than a filled hollow probe or solid probe precisely because it is hollow, so that only the thickness of the end portion of the cylinder comprising the hollow probe actually contacts the blood sample. The column of only slightly compressible air trapped in the end of the hollow probe is also capable of imparting force-induced energy to the blood sample, but this will still be substantially less than the force-induced energy which is imparted by a filled hollow probe or a solid probe.

As indicated, a solid probe, i.e., one made of a single material without any cavities, is also suitable for use in the present invention. The materials from which such solid probes may be fabricated are the same materials as were described above for construction of suitable sealed hollow probes. The density and elasticity of the material which is chosen for fabricating the solid probe will be largely determinative of any variation in the force-induced energy input level to the blood sample, assuming that the same oscillating force is applied to the probe by the instrument in all cases. This assumes, however, that the geometry of the solid probe is that of a simple cylinder, the end plane of which is perpendicular to its main axis. Other geometries are useful, and will also provide variable force-induced energy input levels, as is the case with the hollow probe and the filled probe. For example, a truncated cylinder may be chosen as the spatial form for the probe, or it may be pointed, i.e., a sharp, narrowly rounded tip. The probe does not have to be cylindrical in form, having a circular cross section, but may have an elliptical cross section, or may be a rectilinear solid having a square, octagonal or other cross section. The surface characteristics of the probe may also be varied as well. The surface may be smooth or have varying degrees of roughness. The surface may also be provided with projections of various types and sizes, e.g., pointed or threaded projections, fins and baffles. The surface of the probe may also be coated or impregnated with various materials, e.g., antigens, antibodies, immune cells, and platelet or other blood cell viscosity activators or inhibitors which promote or inhibit changes in the blood sample with regard to its relative viscosity.

It is theorized that the solid exciter-rod probe displaces more of the fluid sample with every stroke of its longitudinal vibration than would be the case where the exciter-rod probe has a hollow configuration, and is as a consequence able to impart a greater amount of force-induced energy to the fluid sample. With a greater amount of force-induced energy input comes a correspondingly greater force-induced energy output, and thus a higher degree of sensitivity from the same sensing means. It is preferred to use the SONOCLOT® Analyzer. However, it is also within the scope of the present invention to employ other devices which are capable of providing the same viscosity signature analysis and measurements as are required for the present invention, preferably using a single instrument.

Figure 2:
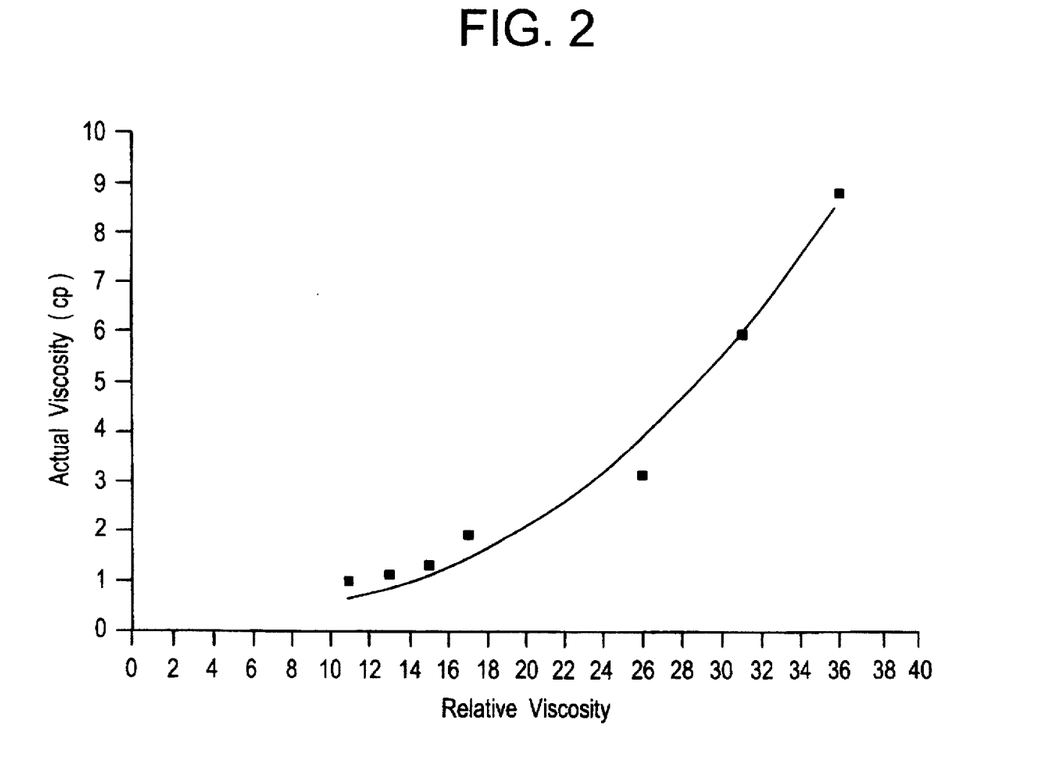
FIG. 2 depicts a curve useful as a chart for converting relative viscosity values to actual viscosity values.

FIG. 2 is a typical graphic plot of relative viscosity on the y-axis versus time (in minutes) on the x-axis. The curve produced by the data points obtained from the viscosity analysis of a blood sample yields important information in a number of regards.

Utilizing the increased sensitivity probes of the present invention, it is possible to obtain readings for the initial and maximum relative viscosity levels of a blood sample, not hitherto observable by any other means. These values, when determined for a normal population in a study, provide a benchmark or baseline to which the values from patients in the same study can then be compared. The values obtained with the increased sensitivity probe establish enhanced or newly visible markers of existing or incipient pathology in the patients providing the blood samples, especially when viewed in the context of the values obtained from normal subjects.

The discussion herein has focused on increased sensitivity, with reference to "higher" force-induced energy input using the probes of the present invention. These comparative terms have been employed because some variation in force-induced energy input is permissible, so long as it results in data which provides a basis for differentiation among patient and normal subject populations with respect to some condition or pathology. Ample guidance is provided herein with regard to the levels which are required for differentiation regarding specific conditions. With this guidance, the artisan can readily determine the optimal force-induced energy input necessary to obtain adequate differentiation.

DESCRIPTION OF PREFERRED EMBODIMENTS

The following Examples are illustrative of the methods and devices of the present invention, and as such are not intended to be in any way a limitation of the scope of the present invention.

EXAMPLE 1

Relative Viscosity Using Probes Providing Increased Sensitivity

A 1.0 ml sample of citrated whole blood was brought up to 37° C. The sample was then gently mixed and 300 µl aliquots were pipetted into the cuvettes of two SONOCLOT® Analyzers, each cuvette containing a small magnetic stirrer. One of the SONOCLOT® Analyzers was equipped with a hollow probe, while the other was equipped with the same hollow probe sealed with bone wax supplied by ETHICON®. The samples were mixed and then the relative viscosity for both samples was obtained as an automatic readout on the instrument chart. The relative viscosity for the sample measured with the sealed hollow probe was significantly increased when compared to the standard hollow probe. The data obtained from these assays was analyzed in various ways, including variation in sensitivity of the instrument. Values obtained for seven (7) blood samples had the mean values ± standard deviations shown in the table of values below.

| | Hollow Probe | Hollow Probe | Bone Wax Sealed Probe | Bone Wax Sealed Probe |
|---|---|---|---|---|
| RELATIVE VISCOSITY VALUES USING PROBES WHICH PROVIDE INCREASED SENSITIVITY; AND STATISTICAL SIGNIFICANCE | | | | |
| SONOCLOT ® Analyzer Sensitivity | 60 (Instrument reading) | 100 (Instrument reading) | 60 (Instrument reading) | 100 (Instrument reading) |

-continued

RELATIVE VISCOSITY VALUES USING PROBES WHICH PROVIDE INCREASED SENSITIVITY; AND STATISTICAL SIGNIFICANCE

|  | Hollow Probe | Hollow Probe | Bone Wax Sealed Probe | Bone Wax Sealed Probe |
|---|---|---|---|---|
| SONOCLOT® Analyzer Reading | 11.4 ± 1.8 | 14.7 ± 2.7 | 28.1 ± 6.0 | 45.6 ± 6.5 |
| Significance |  | p < .001 |  | p < .0001 |

Statistical significance of the data was determined using the paired t-test, with a "p" value of < .05 being considered a showing of significance. At increased sensitivity settings, both probes have greater mean values for the instrument reading of relative viscosity. However, the percent change in the hollow probe readings from the "60" to the "100" setting was only a 28.9% increase, whereas in the case of the bone wax sealed hollow probe the value increased by 62.3%, showing that the bone wax sealed hollow probe provides greater sensitivity and correspondingly improved relative viscosity values compared to those obtained with the hollow probe.

EXAMPLE 2

Evaluation of Reproducibility of Results

In order to determine the reproducibility of the relative viscosity readings obtained in these examples, two aliquots of the same citrated whole blood sample were determined simultaneously using two different SONOCLOT® Analyzers. The amplitude of the curve obtained with wax sealed probes when the instrument head was closed is the relative viscosity, which could be read directly from the instrument or from a chart recorder. Values obtained for the samples had the mean values ± standard deviations shown in the table of values below.

| REPRODUCIBILITY | | |
|---|---|---|
|  | SONOCLOT® Analyzer I | SONOCLOT® Analyzer II |
| Mean | 30.8 | 30.5 |
| SD | 7.6 | 7.3 |
| Number of points | 32 | 32 |
| Significance | p = 0.80 | |

The data in the table above shows that there was no significant difference in the relative viscosity values as determined simultaneously on two different instruments of the same type using aliquots of the same whole blood sample.

EXAMPLE 3

Impact of Different Sealing Materials on Relative Viscosity Values

A study was undertaken to evaluate the impact on relative viscosity values of using different materials used to seal the lower energy input hollow probe in order to produce the higher energy input solid probe. The sealing materials were bone wax obtained from Ethicon® of New Brunswick, N.J., and extra tough pink base dental wax obtained from Hygenic Corporation. The standard hollow probe was pressed into the bone wax or dipped into melted dental wax in order to produce the sealed probes. In order to determine whether or not there was any significant difference in the relative viscosity values obtained with these different probes, duplicate determinations on ten (10) samples of whole blood were carried out. Values obtained for the samples had the mean values ± standard deviations shown in the table of values below.

| RELATIVE VISCOSITY ± SD | |
|---|---|
| Probe Sealed with Bone Wax | Probe Sealed with Dental Wax |
| 35.6 ± 4.9 | 34.6 ± 5.5 |
| p = 0.62 (NS) | |

It was found that there was no significant difference in the relative viscosity determinations whether bone wax or dental wax was used to produce the sealed probes.

EXAMPLE 4

Relative Viscosity as a Quantifier of Hemodilution

In order to study the impact of hemodilution on relative viscosity values, packed red blood cells (RBC) were diluted to form samples of 100% RBC, 90% RBC, and 80% RBC. The diluted samples were prepared by adding physiologic saline (0.9% NaCl) to the RBC's. The relative viscosities of ten (10) different RBC samples were determined, and the values obtained for the samples had the mean values ± standard deviations shown in the table of values below.

| RELATIVE VISCOSITY ± SD | | | |
|---|---|---|---|
| Sample Group | 100% RBC | 90% RBC | 80% RBC |
| Relative Viscosity ± SD | 44.6 ± 9.9 | 39.0 ± 5.3 | 31.8 ± 7.7 |
| Significance |  | p < .01 | p < .001 |

The data in the table above shows that there was a significant decrease in relative viscosity between the 100% and 90% RBC samples (p<0.01), and between the 90% and 80% RBC samples (p<0.001).

A further study of the impact of hemodilution on relative viscosity values was undertaken using citrate human whole blood (CWB) diluted with physiologic saline to produce 100%, 90% and 80% samples (n=19 blood samples). The values obtained for the nineteen (19) samples had the mean values ± standard deviations shown in the table of values below.

| RELATIVE VISCOSITY ± SD | | | |
|---|---|---|---|
| Sample Group | 100% CWB | 90% CWB | 80% CWB |
| Relative Viscosity ± SD | 34.5 ± 12.6 | 29.0 ±5.0 | 23.2 ±3.3 |
| Significance |  | p < .05 | p < .05 |

The data in the table above shows that there was a significant decrease in relative viscosity between the 100% and 90% CWB samples (p<0.05), and between the 90% and 80% CWB samples (p<0.05). Accordingly, relative viscosity measured in accordance with this procedure is sensitive to hemodilution.

EXAMPLE 5

Comparison of Recalcification Time Values and Relative Viscosity Values

It has already been demonstrated in accordance with the data above that relative viscosity measurement is sensitive to hemodilution. A study was undertaken to determine whether recalcification times of various citrated whole blood (CWB) samples would demonstrate any correlation with relative viscosity values (n=7). The values obtained for the seven (7) samples had the mean values ± standard deviations shown in the table of values below.

| RECALCIFICATION TIME vs. RELATIVE VISCOSITY | |
|---|---|
| Recalcification Time (min) ± SD | Relative Viscosity ± SD |
| 6.9 ± 1.6 | 31.3 ± 4.9 |
| r = 0.34 p = NS | |

The data in the above table indicates that there was no significant correlation between the relative viscosity and the recalcification or clotting times of the CWB samples.

EXAMPLE 6

Calculation of Absolute Viscosity Values

The relative viscosity values determined using a SONOCLOT® Analyzer in accordance with the procedures described further above, can be converted into absolute or actual viscosity values (centipoise) by utilizing the graph demonstrated in FIG. 2. Absolute viscosity values were calibrated by using sucrose and glycerol solutions of known viscosity and then measuring the relative viscosity values on the SONOCLOT® Analyzer.

EXAMPLE 7

Viscometric Modulator-Induced Relative Viscosity Changes—Lipoproteins

The measurement of relative viscosity values is an important parameter in the evaluation of the quality of blood perfusion. A study was undertaken to determine whether a viscometric modulator such as a lipoprotein would alter the relative viscosity values of blood samples in vitro, and whether there would be significant variations in relative viscosity values in the sample population.

To 490 µl aliquots of citrate whole blood (CWB) was added either (1) 10 µl of 1 mg/ml high density lipoprotein (HDL) obtained from Sigma Chemical Co., St. Louis, Mo.; (2) 10 µl of 1 mg/ml low density lipoprotein (LDL)also obtained from Sigma Chemical Co., St. Louis, Mo.; or (3) 10 µl of 0.85% saline as control. The samples were incubated at 37° C. for 3 hrs, after which there were added individually, 300 µl of test solution to a cuvette, and the SONOCLOT® Analyzer head containing a wax filled probe was lowered into the test solution in the cuvette, and the viscosity measurement was carried out. The relative viscosity was determined as the magnitude of the clot signal after the SONOCLOT® Analyzer head was closed. The values obtained for the eleven (11) samples had the mean values ± standard deviations shown in the table of values below.

| RELATIVE VISCOSITY ± SD (n = 11) | | |
|---|---|---|
| Control | HDL | LDL |
| 40.6 ± 8.4 | 32.5 ± 7.2 | 30.1 ± 6.7 |

There was a significant reduction in relative viscosity values for both the HDL and LDL samples (p<0.05) when compared to the control value. However, there was no significant difference (p=NS) between the values for the HDL and LDL samples.

EXAMPLE 8

Viscometric Modulator-Induced Relative Viscosity Changes—Tissue Factor (TF)

Tissue factor (TF) is the biochemical substance responsible for initiating the extrinsic pathway of coagulation. A study was undertaken to determine whether TF can alter the relative viscosity of whole blood samples. To fifteen (15) 490 µl aliquots of citrate whole blood (CWB) was added either (1)10 µl of distilled water or (2) TF (prothrombin time reagent) dissolved in water. The samples were incubated at 37° C. for 10 min, after which the relative viscosity values were determined. The values obtained for the fifteen (15) samples had the mean values ± standard deviations shown in the table of values below.

| MEAN RELATIVE VISCOSITIES ± SD | |
|---|---|
| Control | TF |
| 41.7 ± 15 | 35.1 ± 7.6 |
| p < .01 | |

The data in the table above show that TF significantly reduced the relative viscosity values of the samples. It is theorized that this may be due, at least in part, to aggregation of the cells, which may lower the relative viscosity.

EXAMPLE 9

Viscometric Modulator-Induced Relative Viscosity Changes—Collagen and Endotoxin

Collagen is an aggregating agent for platelets, whereas endotoxin is a cellular activator of, e.g., monocytes. A study was undertaken to determine whether a combination of collagen and endotoxin could alter the relative viscosity in vitro. To 480 µl aliquots of citrate whole blood (CWB) was added either (1) 20 µl of water as control, or (2) 10 µl of 0.5 mg/ml E. coli endotoxin +10 µl of 2 mg/ml soluble collagen. The aliquot samples were capped, mixed, and incubated for 10 min at 37° C., after which the relative viscosity values were determined. The values obtained for the forty (40) samples had the mean values ± standard deviations shown in the table of values below.

| Relative Viscosity ± SD | |
|---|---|
| Control | Endotoxin + Collagen |
| 34.2 ± 7.0 | 38.1 ± 8.8 |
| Significance | 2-tailed paired t-test p < .02 |

The data show that there was a significant increase in relative viscosity values induced by the addition of collagen and endotoxin in this test procedure.

EXAMPLE 10

Effect of Surgery on Viscometric Modulator-Induced Relative Viscosity Values

Citrated whole blood samples (CWB) were drawn from patients prior to surgery and again in the recovery room. Aliquots of these blood samples were placed in plastic vials, brought to 37° C. and incubated for 10 min. Thereafter the viscosity was determined using a dental wax sealed probe with a SONOCLOT® Analyzer.

To 480 μl aliquots of citrate whole blood (CWB) were added to either (1) 20 μl of water as control, or (2) 10 μl of 0.5 mg/ml endotoxin +10 μl of 2 mg/ml of collagen. The samples were then capped, mixed and incubated for 10 min at 37° C., after which the relative viscosity values were determined. The results obtained are set out in the table of values below.

| MEAN RELATIVE VISCOSITY ± SD | | |
|---|---|---|
| | Preoperative | Postoperative |
| Control | 34.6 ± 10 | 31.8 ± 8 |
| Significance | p = NS, no significant difference | |
| Viscometric Modulator (Endotoxin + Collagen) Induced Viscosity Changes | 36.4 ± 5 | 29.5 ± 8 |
| Significance | p < .05, 1-tailed paired t-test | |

There were no significant differences between the preoperative and postoperative relative viscosity values as determined in this evaluation; however, there was a significant decrease in the viscometric modulator-induced viscosity values. It is contemplated that this test is thus useful in a identifying patients having a significant risk of experiencing postoperative complications such as multi-organ failure (MOF), a condition characterized by diminished organ perfusion.

EXAMPLE 11

Clinical Use of Changes in Viscometric Modulator-Induced Relative Viscosity Values—Collagen and Endotoxin Induced Changes in Preoperative Patients Compared to Those in Emergency Room Patients Following the Example 9 procedures, thirty-two (32) whole blood samples obtained from preoperative patients and sixty-six (66) whole blood samples obtained from patients evaluated in an emergency room setting had their relative viscosity values determined. The results obtained are set out in the table of values below.

| MEAN RELATIVE VISCOSITY ± SD | | |
|---|---|---|
| | Preoperative Patients | Emergency Room Patients |
| Control | 34.8 ± 9.8 | 32.9 ± 7.6 |
| Significance (2-tailed unpaired t-test) | p = NS, no significant difference | |
| Viscometric Modulator (Endotoxin + Collagen) Induced Viscosity Changes | 33.2 ± 9.0 | 38.0 ± 8.5 |
| Significance (2-tailed unpaired t-test) | p < .05 | |

The data from the table above show that there was no significant difference between the relative viscosity values of the control samples with respect to the preoperative patients and emergency room patients; but that the viscometric modulator-induced changes in relative viscosity values were significantly greater in the emergency room patient population than they were in the preoperative patient population.

EXAMPLE 12

Clinical Use of Changes in Viscometric Modulator-Induced Relative Viscosity Values—Collagen and Endotoxin Induced Changes in Preoperative Patients Compared to Those in Patients with Stroke The procedures utilized in Example 9 above were used to carry out this study. Thirty-two (32) whole blood samples were obtained from preoperative patients and two (2) samples were obtained from stroke patients. The relative viscosity values were determined, and the results obtained are set out in the table of values below.

| MEAN RELATIVE VISCOSITY ± SD | | |
|---|---|---|
| | Preoperative Patients | Stroke Patients |
| Control | 34.8 ± 9.8 | 45.5 ± 0.7 |
| Viscometric Modulator-Induced (Endotoxin + Collagen) | 33.2 ± 9.0 | 51.0 ± 1.4 |
| Significance (2-tailed unpaired t-test) | p = NS, no significant difference | p < .05 |

Although only two (2) whole blood samples were available for testing from stroke patients, the relative viscosity values obtained for the viscometric modulator-induced changes in relative viscosity for these stroke patients were of a greater magnitude than that of all thirty-two (32) whole blood samples for the preoperative patient population. It is hypothesized that the elevated relative viscosity values shown in the stroke patient population may evidence, in part at least, a cause of the decreased blood flow to the brain which is an essential element of the etiology of stroke.

EXAMPLE 13

Use of Probes for Delivery of Relative Viscosity Modifying Agents to Whole Blood Samples Celite, i.e., diatomaceous earth, is a substance which is utilized as the reagent in known procedures for determining activated clotting times (ACT), as well as other coagulation and immune cell testing methods. A study was undertaken, accordingly, to determine whether a bone wax sealed hollow probe could be employed as the means for delivering viscometric modulators of viscosity to whole blood samples during the measurement of the relative viscosity of those whole blood samples. In order to carry out this study, a bone wax sealed hollow probe was dipped in Celite, which adhered to the surface of the probe. Relative viscosity measurements of aliquots of the same sample of human whole blood were then carried out, one aliquot with a bone wax sealed probe alone, and the other aliquot with a bone wax sealed probe coated with Celite. Five (5) samples of human whole blood were used in the study. The relative viscosity values were determined, and the results obtained are set out in the table of values below.

| MEAN RELATIVE VISCOSITY ± SD | |
|---|---|
| Bone wax sealed hollow probe | Bone wax sealed hollow probe coated with Celite |
| 28.4 ± 1.7 | 23.4 ± 1.8 |
| Significance (2-tailed paired t-test) | p < .05 |

The data in the table above demonstrate that a viscosity altering substance, e.g., a pharmaceutically active agent or a viscometric modulator as defined herein, can be employed in a straightforward manner using the procedures described herein, in order to determine the effect that such an agent has on relative viscosity when acting on whole blood samples. Thus, a relative viscosity elevating or reducing substance may be utilized, and the measured value obtained therewith compared to the value obtained with the same sample using the control probe, i.e., the probe without a coating of the viscosity altering substance.

EXAMPLE 14

Reduction of Relative Viscosity Values In Whole Blood Samples Using Niacin (Nicotinic Acid) As the Viscosity Modifying Agent In Vitro Niacin has been used in the past to treat patients with microcirculatory disturbances such as frostbite and thromboangiitis obliterans (Buerger's disease). Whether this beneficial effect is due to a reduction in the viscosity of the blood has not been determined. Accordingly, an in vitro study was undertaken to determine whether niacin has viscosity reducing properties in whole blood samples.

To eight (8) samples of citrated human whole blood was added niacin dissolved in saline at varying concentrations, or an equal volume of just saline used as a control. The samples were incubated at 37° C. for 10 min and the relative viscosity was measured using probes sealed with dental wax. The results obtained are set out in the table of values below.

| MEAN RELATIVE VISCOSITY ± SD | | | | |
|---|---|---|---|---|
| Control | 0.1 mg/ml N | 0.01 mg/ml N | 0.001 mg/ml N | 0.0001 mg/ml N |
| 36.8 ± 5.3 | 29.6 ± 5.0 | 28.8 ± 4.2 | 27.4 ± 3.9 | 26.3 ± 4.2 |
| Significance (2-tailed paired t-test) | p < .001 for each niacin concentration compared to control | | | |

At the concentrations of niacin used in the procedures described above, which may be obtained readily in the blood in vivo, a significant lowering of the relative viscosity values for the whole blood samples was obtained.

EXAMPLE 15

Reduction of Relative Viscosity Values In Whole Blood Samples Using Nicotine As the Viscosity Modifying Agent In Vitro It is well known that nicotine is not only a putatively addictive substance contained in tobacco smoke, but is highly toxic as well, along with other substances found in tobacco smoke which are deleterious to human health, and which have been linked to the development of heart disease, cancer and lung diseases. The evaluation procedures of the present invention were used to carry out a study to determine whether the impact of nicotine on whole blood viscosity, if any, could be measured. To 490 of citrated whole blood was added 10 μl of water as a control, and 10 μl of nicotine solutions to yield final concentrations of nicotine in the whole blood sample of 10 ng/ml and 20 ng/ml. The six (6) samples were incubated 10 minutes at 37° C. and the relative viscosity was determined using a dental wax sealed hollow probe. The results obtained are set out in the table of values below.

| MEAN RELATIVE VISCOSITY ± SD | | |
|---|---|---|
| Control | 10 ng/ml | 20 ng/ml |
| 33.0 ± 5.8 | 41.7 ± 5.6 | 51.3 ± 7.6 |
| Significance (2-tailed paired t-test) | p < .01 | p < .01 |

On an in vitro basis, nicotine at the whole blood concentrations used, which are consistent with concentrations normally found in vivo in the blood of smokers, was found to significantly elevate the viscosity of citrated whole blood. It is theorized that this result may at least partially explain some of the detrimental effects of nicotine seen in humans.

What is claimed is:

1. A method of analyzing one or more samples of a body fluid from a mammal by determining whether or not there is a significant difference or change in comparative determinants of viscosity in said body fluid sample of said mammal, said comparative determinants being derived using a probe which provides increased sensitivity and correspondingly improved relative viscosity values for samples being tested when used together with a viscosity measuring device, in order to identify the presence or incipiency of a symptomatic or asymptomatic pathology caused by, or relating to, said differences or changes in the comparative determinants of viscosity, comprising:

A. placing a first body fluid sample collected from a mammal in a suitable container;
   B. measuring the relative viscosity of said sample and obtaining data which are comparative determinants of viscosity by using a probe which comprises a hollow tube of glass, ceramic, plastic or metal, an end thereof which enters the sample to be measured, having been sealed with bone wax or dental wax and a viscosity measuring device to give values for the comparative determinants of viscosity for said first sample;
   C. comparing said values to values determined for a second sample obtained from; 1). the same mammal at a different time; 2). from the same mammal under conditions of significantly changed homeostasis of said mammal; 3). from the same mammal at the same time but in the presence of a viscometric modulator; or 4). from the same type of mammal free of pathology; and
   D. identifying the presence or incipiency of a symptomatic or asymptomatic pathology caused by or leading to said differences or changes in the values of the comparative determinants of viscosity, by analysis of said values.

2. A method according to claim 1 wherein a vehicle is used with said first and said second samples.

3. A method according to claim 2 wherein said probe comprises a hollow tube of plastic, the end thereof which enters the sample to be measured, having been sealed with bone wax.

4. A method according to claim 2 wherein said vehicle comprises a physiological saline solution.

5. A method according to claim 1 wherein said first and second body fluid an exudate or transudate comprising cerebro-spinal fluid, drainage fluid from one or more body organs or natural or adventitious cavities, or a hematologic fluid.

6. A method according to claim 5 wherein said first and second body fluid samples or hematologic fluid.

7. A method according to claim 6 wherein said hematologic fluid is whole blood.

8. A method according to claim 7 wherein said first and second samples of whole blood are anticoagulated and are prepared by mixing said whole blood with an anticoagulating agent selected from the group consisting of sodium citrate, sodium oxalate, heparin and EDTA; and further thereafter, incubating said first and second samples at from about 35° C. to about 40° C. for from about 1 to about 20 minutes; and then measuring said relative viscosity of said first and second samples using said probe.

9. A method according to claim 8 wherein said incubation is carried out for from about 5 to about 10 minutes.

10. A method according to claim 8 wherein said incubation of said first and second samples is carried out at about 37° C.

11. A method according to claim 7 wherein an anticoagulating agent is not utilized, and said relative viscosity in said first or second sample is measured within from about 0.1 to about 1.0 minute after said whole blood sample has been collected from said mammal.

12. A method according to claim 11 which additionally comprises placing a viscometric modulator together with said first or second sample.

13. A method according to claim 12 wherein said viscometric modulator is present in a concentration of from about 10 μg/ml to about 50 μg/ml of said first or second sample.

14. A method according to claim 12 wherein said viscometric modulator comprises one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

15. A method according to claim 14 wherein said viscometric modulator is an endotoxin or a collagen.

16. A method according to claim 1 which additionally comprises placing, a viscometric modulator together with said first or second samples, thereafter incubating said first and second samples at from about 35° C. to about 40° C. for from about 1 to about 20 minutes.

17. A method according to claim 16 wherein said viscometric modulator is present in a concentration of from about 10 μg/ml to about 50 μg/ml of said first or second sample.

18. A method according to claim 16 wherein said viscometric modulator comprises one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

19. A method according to claim 18 wherein said viscometric modulator is an endotoxin or a collagen.

20. A method according to claim 16 wherein said incubation of said first and second samples is carried out at about 37° C.

21. A method according to claim 16 wherein said incubating of said first and second samples takes place for from about 5 to about 10 minutes.

22. A method according to claim 1 wherein said mammal is *homo sapiens*.

23. A prepackaged diagnostic kit for use together with a viscosity measuring device for analyzing one or more samples of a body fluid to be taken from a mammal for determination of whether or not there is a significant difference or change in comparative determinants of viscosity in said body fluid sample of said mammal, said comparative determinants being derived using a probe which provides increased sensitivity and correspondingly improved relative viscosity values for said one or more samples being tested when used together with said viscosity measuring device, in order to identify a presence or incipiency of a symptomatic or asymptomatic pathology caused by or leading to said differences or change in said comparative determinants of viscosity comprising;

A. at least one first container and at least one second container suitable for receiving aliquots of said body fluid to serve as control and active aliquots, respectively, for measuring relative viscosity when used together with said viscosity measuring device, and for obtaining data which are comparative determinants of viscosity for said control and active aliquots;

B. a probe used together with said viscosity measuring device which comprises a hollow tube of glass, ceramic, plastic or metal, an end thereof which enters the control or active aliquot to be measured, having been sealed with bone wax or dental wax; and C. a diagnostic protocol for determination of said presence or incipiency of said symptomatic or asymptomatic pathology caused by or leading to said differences or changes in said comparative determinants of viscosity, comprising means for analysis of said comparative determinants of viscosity for said control and active aliquots, wherein said relative viscosity and said compatative determinants of viscosity for said control and active aliquots are obtained;

(1) at different times from said mammal, (2) under conditions of significantly changed homeostasis of said mammal, (3) in the absence or presence of, respectively, a viscometric modulator, (4) from the same type of mammal in a healthy state, free of the presence or incipiency of said pathology, and from said mammal being tested, respectively, or any combination of (1)–(4) above.

24. A prepackaged diagnostic kit according to claim 23 wherein said probe comprises a hollow tube of plastic, said end thereof which enters said aliquot to be measured, having been sealed with bone wax.

25. A prepackaged diagnostic kit according to claim 23 wherein said body fluid is an exudate or transudate comprising cerebro-spinal fluid, drainage fluid from one or more body organs or natural or adventitious cavities, or an hematologic fluid.

26. A prepackaged diagnostic kit according to claim 25 wherein said body fluid is a hematologic fluid.

27. A prepackaged diagnostic kit according to claim 26 wherein said hematologic fluid is whole blood.

28. A prepackaged diagnostic kit according to claim 27 wherein:

said at least one first container has a predetermined amount of a preselected anticoagulating agent therein for preparing one or more anticoagulated aliquots of said whole blood sample to serve as control aliquot(s);

said at least one second container has a predetermined amount of said preselected anticoagulating agent therein for preparing one or more anticoagulated aliquots of said whole blood sample to serve as active aliquot(s) ; and said diagnostic protocol comprises means for analysis of said comparative determinants of viscosity of said control and active aliquots of a sample, and includes incubating said control and active aliquots at from about 35° C. to about 40 ° C. for from about 1 to about 20 minutes.

29. A prepackaged diagnostic kit according to claim 28 wherein said preselected anticoagulating agent is one or more members selected from the group consisting of sodium citrate, sodium oxalate, heparin and EDTA.

30. A prepackaged diagnostic kit according to claim 28 wherein said at least one first and second container additionally comprise a predetermined amount of a preselected viscometric modulator for use together with said control and active aliquots.

31. A prepackaged diagnostic kit according to claim 30 wherein said viscometric modulator in said at least one first and second containers is present in a concentration of from about 10 µg/ml to about 50 µg/ml of anticoagulated whole blood.

32. A prepackaged diagnostic kit according to claim 30 wherein said viscometric modulator comprises one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

33. A prepackaged diagnostic kit according to claim 32 wherein said viscometric modulator is an endotoxin or a collagen.

34. A prepackaged diagnostic kit according to claim 28 wherein said diagnostic protocol indicates that incubation of said control and said active aliquots is to be carried out at about 37° C.

35. A prepackaged diagnostic kit according to claim 34 wherein there is further provided in said kit a heating means for obtaining and maintaining incubation temperature.

36. A prepackaged diagnostic kit according to claim 28 wherein said anticoagulant agent is eliminated from said at least one first and second container, and said diagnostic protocol indicates that said incubating of said control aliquot and said active aliquot is to be carried out for from about 1 to about 20 minutes, and that this step is to be carried out within from about 0.1 to about 1.0 minute after said one or more samples of body fluid has been taken from said mammal.

37. A prepackaged diagnostic kit according to claim 27 wherein said at least one second container additionally comprises a predetermined amount of a preselected viscometric modulator for use together with said active aliquot.

38. A prepackaged diagnostic kit according to claim 37 wherein said viscometric modulator in said at least one second container is present in an amount which will result in a concentration of from about 10 µg/ml to about 50 µg/ml of anticoagulated whole blood.

39. A prepackaged diagnostic kit according to claim 37 wherein said viscometric modulator comprises one or more members selected from the group consisting essentially of immunomodulators, exogenous endotoxins, viruses, interferons, phorbol esters, collagens, anticoagulants, platelet and cellular activating factors such as platelet activating factor (PAF) and tumor necrosis factor (TNF), various growth factors, nicotine and nicotinic acid, carrageenans, lipoproteins such as low density lipoprotein (LDL) and high density lipoprotein (HDL), adjuvant peptides, thromboplastins, antigens, myelin, gram negative bacteria, lectins, mitogens, platelet and cellular mediators, chemical modulators, and endogenous substances with the same or substantially similar activities.

40. A prepackaged diagnostic kit according to claim 39 wherein said viscometric modulator is an endotoxin or a collagen.

41. A prepackaged diagnostic kit according to claim 23 wherein said at least one first container and at least one second container additionally contain a vehicle which comprises a physiological saline solution.

42. A prepackaged diagnostic kit according to claim 23 wherein said probe has coated thereon a predetermined amount of a preselected viscometric modulator before being introduced into said aliquot to be measured.

43. A prepackaged diagnostic kit according to claim 42 wherein said predetermined amount of said preselected viscometric modulator is an exotoxin or a collagen.

44. A prepackaged diagnostic kit according to claim 42 wherein said predetermined amount of said preselected viscometric modulator is provided in a separate container from which it is then applied to and coated on said probe.

45. A probe which provides increased sensitivity and corresponding improved relative viscosity values for a sample of a body fluid, when used together with a viscosity measuring device comprising a hollow tube of glass, ceramic, plastic or metal, an end thereof which enters a sample to be measured, having been sealed with bone wax or dental wax, said probe additionally having coated thereon a predetermined amount of a preselected viscometric modulator.

* * * * *

UNITED STATES PATENT AND TRADEMARK OFFICE
CERTIFICATE OF CORRECTION

PATENT NO. : 5,792,660
DATED : August 11, 1998
INVENTOR(S) : Spillert et al.

It is certified that error appears in the above-identified patent and that said Letters Patent is hereby corrected as shown below:

Column 30, claim 43, line 3 "exotoxin" should read --endotoxin --.

Signed and Sealed this

Sixteenth Day of February, 1999

Attest:

Attesting Officer

Acting Commissioner of Patents and Trademarks